(12) United States Patent
Merk et al.

(10) Patent No.: US 9,085,054 B2
(45) Date of Patent: Jul. 21, 2015

(54) METHOD OF TEXTURING AN INNER SURFACE OF A SELF-EXPANDING IMPLANT DELIVERY SYSTEM OUTER SHEATH

(71) Applicant: Cook Medical Technologies LLC, Bloomington, IN (US)

(72) Inventors: James C. Merk, Terre Haute, IN (US); Nathaniel A. Irwin, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 301 days.

(21) Appl. No.: 13/724,071

(22) Filed: Dec. 21, 2012

(65) Prior Publication Data

US 2014/0173878 A1    Jun. 26, 2014

(51) Int. Cl.
*A61F 2/95*    (2013.01)
*B23P 11/00*    (2006.01)
*A61F 2/966*    (2013.01)

(52) U.S. Cl.
CPC . *B23P 11/00* (2013.01); *A61F 2/95* (2013.01); *A61F 2002/9665* (2013.01); *A61F 2240/001* (2013.01); *Y10T 29/49863* (2015.01)

(58) Field of Classification Search
CPC .............. A61F 2/95; A61F 2002/9665; A61F 2240/001; A61F 2013/15715; B23P 11/00; B23P 11/005; Y10T 29/49863
See application file for complete search history.

(56) References Cited

U.S. PATENT DOCUMENTS

| | | | |
|---|---|---|---|
| 5,554,181 A | 9/1996 | Das | |
| 6,136,006 A | 10/2000 | Johnson et al. | |
| 6,299,635 B1 | 10/2001 | Frantzen | |
| 6,520,986 B2 | 2/2003 | Martin et al. | |
| 6,769,161 B2 | 8/2004 | Brown et al. | |
| 6,790,225 B1 | 9/2004 | Shannon et al. | |
| 6,859,986 B2 | 3/2005 | Jackson et al. | |
| 6,911,041 B1 | 6/2005 | Zscheeg | |
| 7,223,280 B2 | 5/2007 | Anson et al. | |
| 7,526,849 B2 | 5/2009 | Serrano | |
| 7,959,664 B2 | 6/2011 | Richter | |
| 8,042,251 B2 | 10/2011 | Asmus et al. | |
| 8,062,351 B2 | 11/2011 | Burnside et al. | |
| 2002/0017503 A1* | 2/2002 | Banas et al. | 219/69.11 |
| 2003/0018343 A1 | 1/2003 | Mathis | |
| 2005/0228489 A1* | 10/2005 | Kujawski | 623/1.28 |
| 2006/0100687 A1 | 5/2006 | Fahey et al. | |
| 2008/0161902 A1 | 7/2008 | Poulsen | |
| 2009/0192593 A1 | 7/2009 | Meyer et al. | |
| 2010/0145429 A1* | 6/2010 | Dhoke et al. | 623/1.11 |
| 2010/0249912 A1* | 9/2010 | Gibbons et al. | 623/1.38 |

FOREIGN PATENT DOCUMENTS

WO    WO 9949790    10/1999

* cited by examiner

*Primary Examiner* — Alexander P Taousakis
(74) *Attorney, Agent, or Firm* — Brinks Gilson & Lione; Eric D. Babych

(57) ABSTRACT

A method of forming a textured surface on the inner surface of a sheath is provided. The sheath may be used in a delivery system to restrain a self-expanding medical implant in a compressed state. In the method, a sleeve is squeezed against a textured pattern on a mandrel to form a textured surface on the inner surface of the mandrel. The diameter of the mandrel is then contracted before the mandrel is removed from the sleeve.

22 Claims, 2 Drawing Sheets

METHOD OF TEXTURING AN INNER SURFACE OF A SELF-EXPANDING IMPLANT DELIVERY SYSTEM OUTER SHEATH

BACKGROUND

The present invention relates generally to medical devices and more particularly to delivery systems for medical devices.

Intraluminal medical devices are used by physicians to treat numerous conditions using minimally invasive procedures. Examples of intraluminal medical devices include stents, stent-grafts, filters, valves, etc. One type of intraluminal medical device that has become especially common is self-expanding stents. Typically, self-expanding medical devices, including stents, are made from an elastic structure that may be compressed into a low profile state that can be passed through vessels in a patient with minimal trauma. Once at the desired treatment site, the self-expanding medical device is released and self-expands like a spring until it contacts a tissue wall which prevents further expansion. Common materials that are used in self-expanding medical devices include nitinol and stainless steel, although other materials are also possible.

Self-expanding stents are used to treat various organs, such as the vascular system, colon, biliary tract, urinary tract, esophagus, trachea and the like. For example, stents are commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

One type of delivery system for intraluminal medical devices includes an inner catheter and an outer sheath attached to a handle arrangement. One portion of the handle is typically connected to the inner catheter and another portion of the handle is typically connected to the outer sheath. The inner catheter extends coaxially through the outer sheath, and the two portions of the handle are arranged to longitudinally pull the outer sheath relative to the inner catheter. Thus, when the distal end of the delivery system is positioned within the patient's body at the intended treatment site, the physician actuates the handle outside the patient's body by moving the two portions relative to each other so that the outer sheath is withdrawn over the medical device and inner catheter. In the case of self-expanding medical devices, like stents, the outer sheath also serves to radially restrain the device in the compressed state until the outer sheath is withdrawn. As the outer sheath is withdrawn, the medical device is released in the body at the treatment site, and in the case of a self-expanding stent, the stent expands outward away from the inner catheter and presses against the vessel wall. Although the outer sheath is usually withdrawn by pulling the outer sheath proximally relative to the inner catheter, it may also be possible to withdraw the outer sheath by pushing the inner catheter distally relative to the outer sheath. After the medical device has been fully released from the delivery system, the handle may then be pulled by the physician to withdraw the inner catheter and outer sheath from the patient's body, while leaving the medical device implanted in the body.

Precise placement of intraluminal medical devices is a concern in most medical procedures. One problem that can contribute to imprecise placement of intraluminal medical devices is deflection of the delivery system during deployment. This can be a particular problem in the deployment of self-expanding medical devices, like stents, because the medical device presses outward against the inner surface of the outer sheath prior to deployment. When the outer sheath is withdrawn, the outward pressure exerted by the medical device creates friction between the medical device and the outer sheath. Since the medical device is typically prevented from moving proximally with the outer sheath by a stop attached to the inner catheter, the frictional force between the medical device and the outer sheath causes the outer sheath to be in tension and the inner catheter to be in compression. This can cause the inner catheter to contract in length due to the compressive force. In addition, the inner catheter can buckle, or snake, within the outer sheath. Both of these responses can cause the distal end of the inner catheter, and thus the medical device itself, to move proximally from the intended treatment site. Although the contraction and buckling may decrease somewhat as the outer sheath begins to withdraw from the medical device due to the release of some of the frictional force, the distal end of the inner catheter may not completely return to the intended treatment site when the medical device is initially released and implants within the patient's body. Moreover, the stent and/or inner catheter can build up sufficient spring force due to the contraction of the inner catheter and the stent to cause the stent to jump distally once the static friction is released. With medical devices that cause high frictional loads against the outer sheath, like drug coated stents, covered stents and particularly long stents, the initial deflection of the delivery system and subsequent distal movement due to the release of friction can make it difficult for a physician to predict the exact location where the medical device will be released in a patient's body.

One possible way to improve the positioning accuracy of self-expanding implant delivery systems is to reduce the friction that occurs between the self-expanding medical device and the outer sheath. One proposal for reducing friction is to texture the inner surface of the outer sheath so that the inner surface is non-smooth. That is, the inner surface of the outer sheath that contacts the outer surface of the medical device prior to deployment could have alternating or interwoven recessed and raised regions. As a result, the medical device primarily presses against the raised regions (i.e., the regions protruding closer toward the axis of the outer sheath), while the recessed regions reduce the contact area between the medical device and the outer sheath. It is believed that a textured inner surface on the outer sheath may result in reduced friction and less overall deflection of the delivery system compared to an outer sheath with a smooth inner surface.

However, forming a textured surface on the inner surface of an outer sheath is a difficult process that has limited the use of this possible improvement in self-expanding implant delivery systems. For example, while methods for texturing outer surfaces like cylindrical rods and tubes are relatively straightforward, forming a textured surface inside the lumen of a small sheath is much more difficult.

Accordingly, the inventors believe it would be desirable to provide a manufacturing method for forming a textured surface on the inner surface of a sheath.

SUMMARY

A method is described for forming a textured surface on the inner surface of a sheath. A sleeve is disposed on a mandrel having a textured pattern on an outer surface thereof. The sleeve is then squeezed against the mandrel to form a textured surface on the inner surface of the sleeve. After the textured surface is formed, the diameter of the mandrel is contracted and the mandrel is withdrawn from the sleeve. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the, following description in conjunction with the drawings, in which.

DETAILED DESCRIPTION

Figure 1:
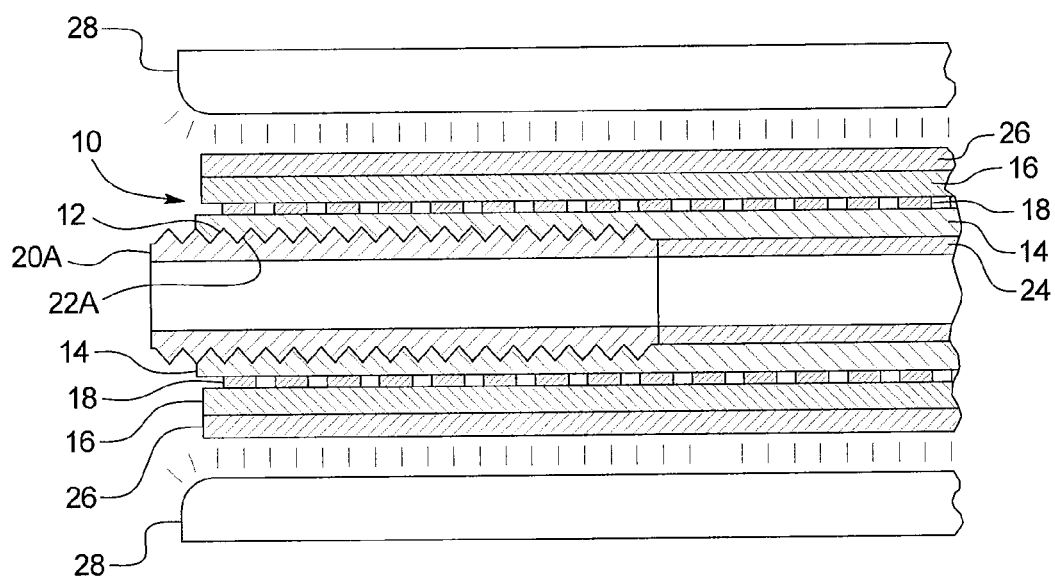
FIG. 1 is a cross-sectional view of a method of making a sheath with a textured inner surface.

Referring now to the figures, and particularly to FIG. 1, a cross-sectional view of a sheath 10 being formed with a texture 12 along at least a portion of the inner surface of the sheath 10 is shown. While the sheath 10 is preferably envisioned as an outer sheath 10 for a self-expanding implant delivery system, it is possible that the textured sheath 10 may be useful in other devices as well. The sheath 10 may be made up of one or more layers 14, 16, or sleeves 14, 16, and may include various types of reinforcement structures 16 if desired. For example, in the embodiment shown in FIG. 1, the sheath 10 may have an inner sleeve 14 and an outer sleeve 16 with a reinforcement structure 18, such as a coil or a braid, between the inner and outer sleeves 14, 16.

Preferably, the inner sleeve 14 has a higher melting temperature than the outer sleeve 16. For example, the inner sleeve 14 may be made from a polymeric material, such as polytetrafluoroethylene (PTFE), ethylene tetrafluoroethylene (ETFE), fluorinated ethylene propylene (FEP), propylene or polyethylene. Preferably, the melting temperature of the inner sleeve 14 is about 600° F. to about 700° F. By contrast, the outer sleeve 16 may be made from a thermoplastic material, like nylon, with a lower melting temperature of about 300° F. to about 500° F. The reinforcement structure 18 is preferably made from a metal, such as stainless steel.

Figure 2A:
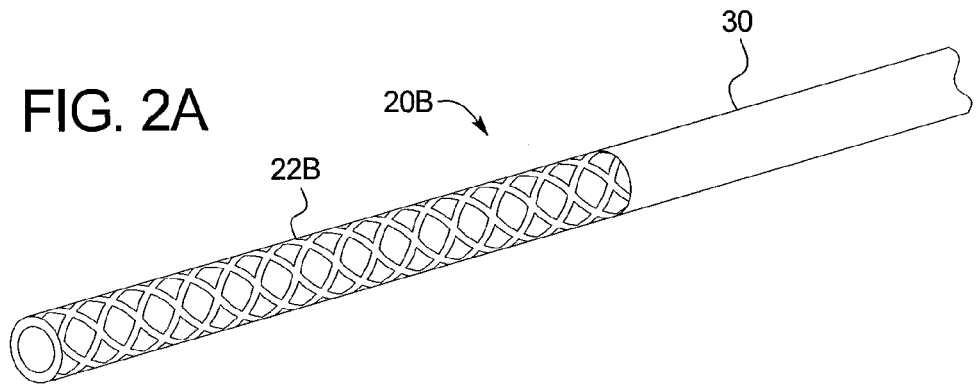
FIG. 2A is a perspective view of a mandrel with a solid wall and a textured section.
Figure 2B:
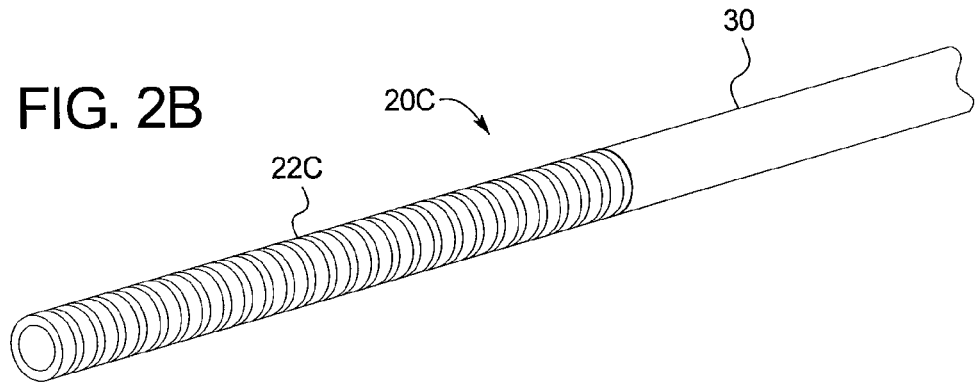
FIG. 2B is a perspective view of another mandrel with a solid wall and a different textured section.

If the sheath 10 is formed of multiple sleeves 14, 16, the sleeves 14, 16 may be melt bonded together at the same time that a texture 12 is formed on the inner surface of the inner sleeve 14. As shown in FIG. 1, a first mandrel 20A is inserted through the lumen of the inner sleeve 14. The first mandrel 20A is provided with a textured pattern 22A on the outer surface. Preferably, the textured pattern 22 on the outer surface of the mandrel 20 contacts at least 70%, and more preferably 90%, of the inner surface of the inner sleeve 14 along a length of at least half as long as the overall length of the self-expanding implant that will be loaded into the sheath 10. In other words, at least half of the self-expanding implant will contact the textured surface 12 of the implant, and more preferably, the textured surface 12 will contact substantially the entire length of the implant. In addition, unlike a coiled forming wire or the like, the mandrel 20 contacts substantially the entire circumference and length of the textured surface 12 of the sheath 10. That is, the mandrel preferably contacts at least 70% of the textured surface 12, or more preferably at least 90% of the textured surface 12. For instance, in the embodiment of FIGS. 2A-2B, the mandrel 20B-C preferably contacts 100% of the textured surface 12. By contrast, in the embodiment of FIGS. 3A-3B, a small portion of the textured surface 12 may be formed by the slots 32 where the textured surface 12 is not in immediate contact with the mandrel 20D. However, even the mandrel 20D of FIGS. 3A-3B contacts at least 70%, and more preferably 90%, of the textured surface 12 in contrast to forming wires and the like.

Where the textured surface 12 is only being formed in the distal end of an elongated outer sheath 10, the first mandrel 20A may only extend along the distal portion of the inner sleeve 14. If desired, a non-textured second mandrel 24 may be inserted through the proximal portion of the inner sleeve 14. Alternatively, as shown in FIGS. 2A-2B, a single mandrel 20B-C may be used for the length of the inner sleeve 14 with only the distal section 22B-C of the mandrel 20B-C being textured and proximal section 30 being smooth. In addition, the sheath 10 may be manufactured as two separate sections, one using a textured mandrel 20A and one using a smooth mandrel 24, and the two sections may be bonded together after the two sections have been formed.

Preferably, the inner and outer sleeves 14, 16 are bonded together by sliding a heat shrink tube 26, such as fluorinated ethylene propylene (FEP), over the outer sleeve 16. The heat shrink tube 26 and outer sleeve 16 may then be heated with radiant heat from a heating element 28. Preferably, the outer sleeve 16 is heated to about 350° F. to about 500° F., or more preferably to about 380° F. to about 450° F., which is just far enough above the melting temperature of the outer sleeve 16 to at least partially allow the outer sleeve 16 to melt and flow and to adhere to the inner sleeve 14. Although the inner sleeve 14 may be heated by the heating element 28 also, the melting temperature of the inner sleeve 14 is preferably high enough not to result in substantial melting of the inner sleeve 14. Where the sheath 10 includes a reinforcement structure 18, the outer sleeve 16 preferably flows through the open spaces in the reinforcement structure 18 when melted to adhere to the inner sleeve 14. The outer surface of the inner sleeve 14 may be chemically or mechanically etched to improve bonding between inner and outer sleeves 14, 16.

As the heat shrink tube 26 is heated, the heat shrink tube 26 squeezes the inner and outer sleeves 14, 16 and reinforcement structure 18 against the first and second mandrels 20, 24. In addition to melting the outer sleeve 16 to bond the inner and outer sleeves 14, 16 together, the squeezing of the heat shrink tube 26 also presses the inner surface of the inner sleeve 14 against the textured pattern 22 of the first mandrel 20. As a result, a textured surface 12 is formed on the inner surface of the inner sleeve 14. The textured surface 12 formed on the inner sleeve 14 has a reversed shape compared to the textured pattern 22 of the mandrel 20 in that protrusions on the mandrel 20 form recessed regions in the textured surface 12 and recesses in the textured pattern 22 form raised regions in the textured surface 12 (i.e., portions that extend closer to the axis of the sheath 10). Since the inner sleeve 14 preferably does not melt as the textured surface 12 is formed, the textured surface 12 may be formed by conforming the inner sleeve 14 to the textured pattern 22 of the first mandrel 20. Conforming of the inner sleeve 14 is made possible at least in part due to the thinness of the inner sleeve 14 and the softening of the outer sleeve 16, which allows the outer sleeve 16 to reform around the conformed inner sleeve 14 and retains the inner sleeve 14 in the conformed shape after the inner and outer sleeves 14, 16 have bonded and the first mandrel 20 has been removed. If it is determined that the reinforcement structure 18 interferes with conforming of the inner sleeve 14, the size and shape of the reinforcement structure 18 may be modified to permit the reinforcement structure 18 to conform with the inner sleeve 14' or to provide a larger portion of open space through the reinforcement structure 18 for bonding of the inner and outer sleeves 14, 16. For example, a narrow, flexible, widely spaced reinforcement structure 18 may be desirable. Alternatively, the reinforcement structure 18 may be omitted from the textured section 12. An additional sleeve with a lower melting temperature like the outer sleeve 14 may also be included between the inner sleeve 14 and the reinforcement structure 18.

Typically, the heat shrink tube 26 will be removed from the sheath 10 before the mandrel 20 is removed from the sheath, but it may also be possible to remove the heat shrink tube 26 later or leave the heat shrink tube 26 on the sheath 10. In any event, after the textured surface 12 is formed on the inner surface of the sheath 10, the first mandrel 20 is withdrawn from the lumen of the inner sleeve 14. This is accomplished by contracting the diameter of the outer surface of the mandrel 20 and pulling the mandrel 20 and the sheath 10 apart. Thus, unlike a mandrel that is merely pulled out of the lumen of a sheath without contracting the mandrel, the patterned mandrel 20 is first contracted at least slightly in diameter and preferably remains slightly contracted as it is withdrawn from the sheath 10. The mandrel 20 does not necessarily need to be contracted a large amount to aid in withdrawing the mandrel 20 from the sheath 10. For example, it may be sufficient to contract the mandrel 20 just enough to break the temporary bonding that can occur between the mandrel 20 and the inner surface of the inner sleeve 14 during the pattern 12 forming step. This amount of contraction may be less than the maximum depth of the textured pattern 22 so that the textured pattern 22 does not fully clear the textured surface 12 on the inner sleeve 14 when the mandrel 20 is withdrawn from the sheath 10. However, this amount of contraction may be enough to significantly ease withdrawal of the mandrel 20 since temporary adhesion or bonding between the mandrel 20 and the sleeve 14 can increase the difficulty of removing the mandrel 20. Moreover, the fact that the textured pattern 22 of the mandrel 20 and the textured surface 12 of the sleeve 14 may not clear each other during withdrawal of the mandrel 20 may not be a significant problem because the material of the inner sleeve 14 may be sufficiently elastic to allow the raised regions of the textured surface 12 to elastically deflect as the mandrel 20 is withdrawn without permanently deforming. Also, even when the textured surface 12 of the inner sleeve 14 is required to deflect in order to withdraw the mandrel 20, a small amount of contraction of the mandrel 20 will reduce deflection of the textured surface 12 to ease in withdrawal of the mandrel 20 and will minimize plastic deformation. Thus, even a small amount of contraction of the mandrel 20 will aid in withdrawing the mandrel 20 compared to non-contracting mandrels that are simply pulled out of a sheath without any discernible contraction. In any event, it is preferred that the outer surface of the mandrel 20 contract at least about 0.00025" per side before the mandrel 20 is withdrawn from the sheath 10. In the contemplated mandrels 20B-D described further below, it is also envisioned that the mandrel 20 may be restricted from contracting by more than 0.0025" per side during withdrawal of the mandrel 20.

After the mandrel 20 is withdrawn from the sheath 10, a self-expanding medical implant like a stent may be loaded into the distal end of the sheath 10 in a compressed state using conventional loading methods. Thus, once loaded, the medical implant will be in contact with the textured surface 12 of the inner sleeve 14, which is expected to improve delivery performance of the delivery system.

Turning to FIGS. 2A-2B, the mandrel 20B-C may be a solid tube without any slots or discontinuities that would permit mechanical contraction of the mandrel 20B-C. Thus, the tube 20B-C as a solid wall around the circumference of the tube 20B-C without any separations in the wall or circumference. A tube 20B-C is preferred over a solid rod to permit greater contraction during temperature changes as described below. Also, as noted above, the mandrel 20 may integrate the first and second mandrels 20, 24 described above into a single mandrel 20B-C having a textured section 22B-C and a non-textured section 30. The textured pattern 22 may be any type of pattern that is desirable on the inner surface of a sheath 10. In particular, it is preferable that the pattern 22 provide a textured surface 12 inside the outer sheath 10 of a self-expanding medical device delivery system that reduces friction between the self-expanding implant and outer sheath 10. For example, in FIG. 2A, the mandrel 20B is shown with a pattern 22b of spiral recesses and diamond protrusions, which will result in a textured surface 12 on the inner sleeve 14 having spiral raised regions and diamond depressions, or recessed regions. In FIG. 2B, the mandrel 20C is shown with a pattern 22C of alternating raised and recessed rings.

In one embodiment, the mandrel 20B-C may be made from a material having a coefficient of thermal expansion that causes the mandrel 20B-C to contract when the mandrel 20B-C is cooled. For example, the mandrel 20B-C could be made from aluminum, brass, copper, gold, magnesium, nickel, PVC, a high durometer rubber, silver or stainless steel. It may also be desirable to provide various types of surface treatments on the outer surface of the mandrel 20, such as passivating or anodizing the mandrel 20 when a material like aluminum is used. Preferably, the volumetric coefficient of thermal expansion of the material of the mandrel 20B-C is higher than about 30, and more preferably higher than about 40. In most embodiments, this would exclude materials like glass and ordinary carbon steels that have relatively low coefficients of thermal expansion.

In use, the mandrel 20B-C could be inserted into the inner sleeve 14 at room temperature and the pattern 12 formed as described above. Then, in order to contract the mandrel 20B-C, the mandrel 20B-C may be cooled to cause the diameter of the mandrel 20B-C to contract in response to the coefficient of thermal expansion. In most circumstances, the outer surface of the mandrel 20B-C will contract about 0.00075" or less per side when relying upon the coefficient of thermal expansion to contract the mandrel 20B-C. One way to cool the mandrel 20B-C may be to pump or blow coolant through the lumen of the mandrel 20B-C. For example, liquid nitrogen may be pumped or blown into the mandrel 20B-C. Preferably, the coolant is connected to the opening in the mandrel 20B-C adjacent to the distal opening of the sheath 10 (i.e., the end with the patterned surface 12). If desired, the coolant may be allowed to escape through the opening at the opposite end. Alternatively, a closed-loop system may be designed, where the coolant is collected at the opposite end opening and recirculated. If the cooling of the mandrel 20B-C adversely affects the sheath 10, for example by causing the sheath 10 to contract with the mandrel 20B-C, a coating of an insulating material may be applied to the exterior of the mandrel 20B-C, in addition to any other coatings that may be desired. For example, it may be possible to spray a thin coating of a ceramic material onto the mandrel 20B-C to insulate the sheath 10 from the mandrel 20B-C.

In another embodiment, the mandrels 20B-C of FIGS. 2A-2B could be made from a shape memory material. For example, nitinol with a transformation temperature either below room temperature or above room temperature may be suitable. It is also desirable for the shape memory material to have two-way shape memory, where the diameter of the mandrel 20B-C as a larger remembered state above the transformation temperature and a smaller remembered state below the transformation temperature. In most circumstances, the amount of contraction that may be possible in the mandrel 20B-C will be more than the contraction possible using the coefficient of thermal expansion. Depending on where the transformation temperature is set, the mandrel 20B-C made from a shape memory material may be cooled to contract the mandrel 20B-C either by actively cooling the mandrel 20B-C below room temperature or by allowing the mandrel 20B-C to naturally cool down to room temperature. In both situations, the temperature of the mandrel 20B-C should be above the transformation temperature while the textured surface 12 has been formed so that the diameter of the mandrel 20B-C is in the larger remembered state when the textured surface 12 is formed. If the transformation temperature is below room temperature, the mandrel 20B-C may be actively cooled below the transformation temperature after the sleeve 14 is squeezed onto the mandrel 20B-C to form the textured surface 12. This may be done using similar methods described above in relation to contracting the mandrel 20B-C using the coefficient of thermal expansion. As a result, the mandrel 20B-C contracts to the smaller remembered state as the mandrel 20B-C is cooled below the transformation temperature. Alternatively, if the transformation temperature is above room temperature, the mandrel 20B-C may be heated above the transformation temperature as the textured surface 12 is formed to cause the mandrel 20B-C to expand to its larger remembered state. This may occur due to the heating described above to bond the inner and outer sleeves 14, 16 together and form the textured surface 12, or a separate heating source may be applied directly to the mandrel 20B-C. After the textured surface 12 is formed, the mandrel 20B-C may be allowed to naturally cool down to room temperature, which then causes the temperature to drop below the transformation temperature and causes the mandrel 20B-C to contract to the smaller remembered state.

Figure 3A:
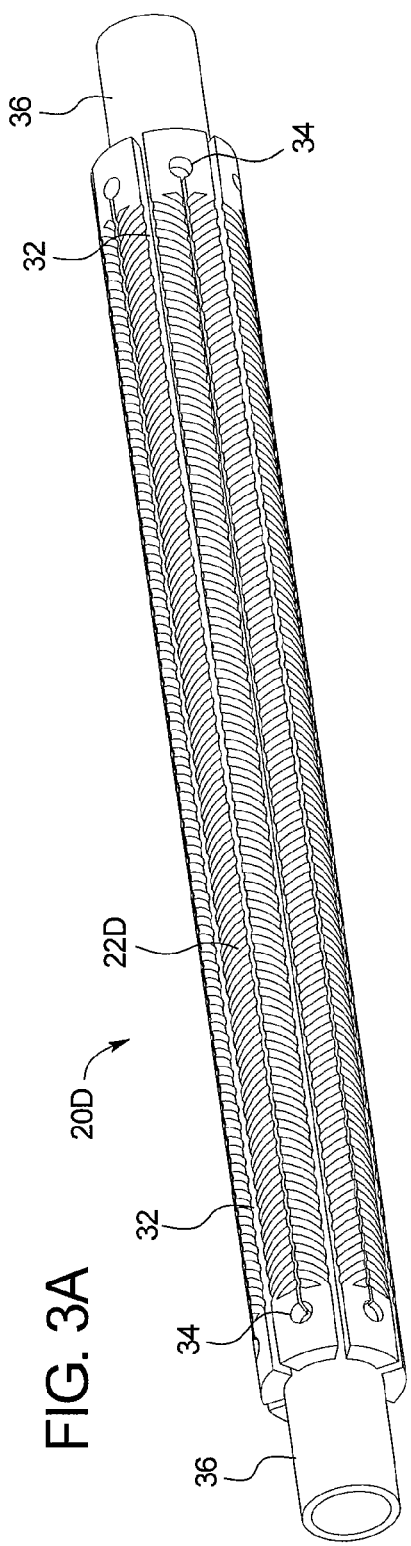
FIG. 3A is a perspective view of a mandrel with slots extending through the wall of the mandrel.
Figure 3B:
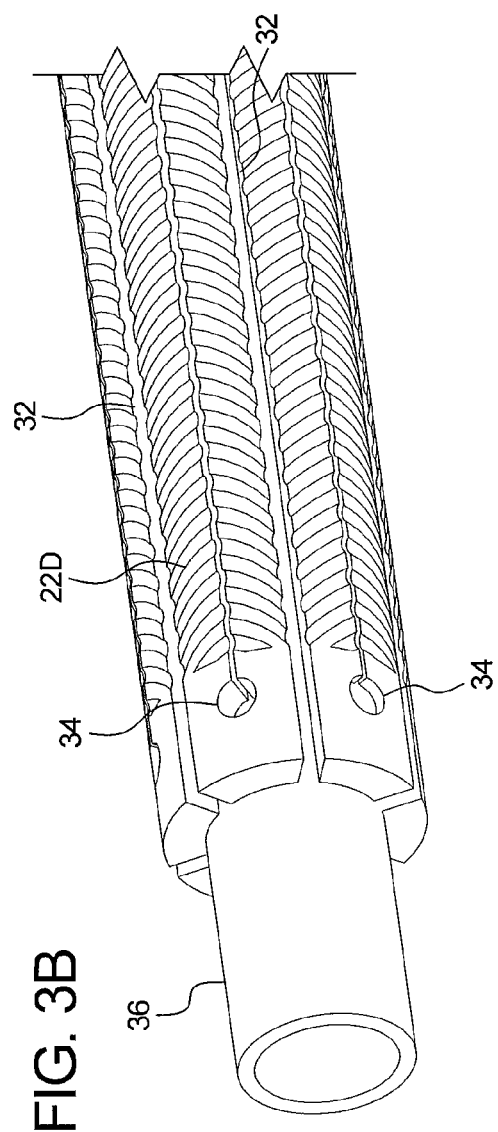
FIG. 3B is a close-up perspective view of the mandrel of FIG. 3A showing the textured outer surface.

Turning to FIGS. 3A-3B, in another embodiment the mandrel 20D may have one or more slots 32 extending through the wall of the mandrel 20D to allow the diameter of the mandrel 20D to mechanically contract by reducing the width of the slots 32. Thus, the tube of the mandrel 20D is non-solid as compared to the mandrels 20B-C of FIGS. 2A-2B. As shown, one end of each slot 32 extends all the way to the end of the mandrel 20D and the other end of each slot 32 may terminate at a strain relief hole 34 before the end of the mandrel 20D. The slots 32 and strain relief 34 may alternate around the circumference of the mandrel 20D so that the interconnected length of the mandrel 20D winds back and forth along the length of the mandrel 20D and around the mandrel 20D. As shown in FIGS. 3A-3B, the mandrel 20D may be expanded in diameter by inserting an inner support member 36 through the lumen of the mandrel 20D. As a result, the slots 32 are forced open to increase the diameter of the mandrel 20D. However, the slots 32 tend to want to close in the relaxed state of the mandrel 20D. Thus, the mandrel 20D is contracted as described above after the textured surface 12 is formed by removing the inner support member 36 from the mandrel 20D. The mandrel 20D then elastically collapses by reducing the width of the slots 32.

Because the slots 32 form part of the textured pattern 22D (i.e., the inner sleeve 14 will tend to conform into each slot 32 to form a raised ridge on the inner surface of the sleeve 10), it is desirable to size the width of the slots 32 to be suitable for the intended textured surface 12. For example, it may be desirable for the width of each slot 32 to be about 0.0015" or less in the expanded state when the textured surface 12 is formed. However, limiting the width of the slots 32 in the expanded state also limits how far the diameter of the mandrel 20D can be contracted when the inner support member 36 is removed, since the slots 32 will fully close with only a small amount of contraction. Thus, in typical circumstances, the mandrel 20D may contract about 0.0015" or less per side when the inner support member 36 is removed.

The textured pattern 22D may be any type of pattern that is desired. However, as shown in FIG. 3B, it may be desirable for the textured pattern 22D to be alternating grooves in the surface of the mandrel 20D that angle away from each of the slots 32. Thus, the slots 32 may form an integral part of the textured pattern 22D with recesses that connect to the slots 32. As a result, the reversed textured surface 12 that is formed in the sheath 10 may have longitudinal ribs interconnected by circumferential ribs. As also shown in FIG. 3B, the textured pattern 22D may terminate before the end of the mandrel 20D and before the strain relief 34. This is possible because one end of the mandrel 20D will usually remain outside of the distal end of the sheath 10 during the forming process so that the mandrel 20D can be gripped to withdraw the mandrel 20D. Thus, the end that remains outside the sheath 10 does not need to be textured. The other end of the mandrel 20D that remains inside the sheath 10 during forming may be positioned proximally from the region where the medical implant will contact the sheath 10. Thus, the strain relief 34 and end of the mandrel 20D need not be positioned in the region of the sheath 10 where the textured surface 12 is desired. Although the strain relief 34 and portions of the slots 32 positioned proximal from the textured pattern 22D may tend to cause a slight amount of texturing to the sheath 10 proximal from the implant, this region is typically located where a proximal stop is located on the inner catheter and where the inner catheter slightly tapers so that a slight amount of texturing on the sheath 10 in this area may not cause significant interference problems.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A method of forming a textured surface on at least a portion of an inner surface of an outer sheath of a self-expanding implant delivery system, wherein the outer sheath restrains the self-expanding implant in a compressed state prior to being released at a treatment site and said textured surface contacts an outer surface of said self-expanding implant in said compressed state, said method comprising:

providing a mandrel with a textured pattern disposed on an outer surface of said mandrel;

disposing a sleeve onto said mandrel, said sleeve comprising said inner surface of said outer sheath;

squeezing said sleeve against said mandrel and said textured pattern, said textured surface thereby being formed on said inner surface of said sleeve, wherein said outer surface of said mandrel contacts at least 70% of said inner surface of said sleeve along a length of at least half an overall length of said self-expanding implant;

contracting a diameter of said outer surface of said mandrel;

withdrawing said mandrel from said sleeve; and loading said self-expanding implant into said sleeve in said compressed state, said textured surface contacting said outer surface of said self-expanding implant in said compressed state.

2. The method according to claim 1, wherein said mandrel contacts at least 70% of said inner surface of said sleeve along substantially an entire length of said self-expanding implant.

3. The method according to claim 1, wherein said outer surface of said mandrel contacts at least 90% of said inner surface of said sleeve along said length of at least half said overall length of said self-expanding implant.

4. The method according to claim 3, wherein said mandrel contacts at least 90% of said inner surface of said sleeve along substantially an entire length of said self-expanding implant.

5. The method according to claim 1, wherein said diameter of said outer surface of said mandrel is restricted from contracting by more than 0.0025" per side during said withdrawing step.

6. The method according to claim 1, further comprising heating said sleeve during said squeezing step.

7. The method according to claim 1, wherein said sleeve comprises a polymeric material.

8. The method according to claim 7, further comprising disposing a thermoplastic sleeve over said sleeve and heating said sleeve and said thermoplastic sleeve while squeezing said sleeve and said thermoplastic sleeve during said squeezing step, wherein said thermoplastic sleeve has a first melting temperature lower than a second melting temperature of said sleeve, said sleeve and said thermoplastic sleeve being heated above said first melting temperature and below said second melting temperature, said thermoplastic sleeve thereby melt forming during said squeezing and said sleeve conforming to said textured pattern without melting.

9. The method according to claim 1, wherein said outer surface of said mandrel contacts at least 90% of said inner surface of said sleeve along said length of at least half said overall length of said self-expanding implant, said mandrel comprises a solid tube made from a material defined by a coefficient of thermal expansion, said contracting step comprising cooling said tube to contract said diameter in response to said coefficient of thermal expansion.

10. The method according to claim 9, wherein said diameter of said outer surface of said mandrel contracts less per side than a maximum depth of said textured pattern, said textured surface elastically deflecting during said withdrawing step without permanently deforming.

11. The method according to claim 10, wherein said sleeve comprises a polymeric material, and further comprising disposing a thermoplastic sleeve over said sleeve and heating said sleeve and said thermoplastic sleeve while squeezing said sleeve and said thermoplastic sleeve during said squeezing step, wherein said thermoplastic sleeve has a first melting temperature lower than a second melting temperature of said sleeve, said sleeve and said thermoplastic sleeve being heated above said first melting temperature and below said second melting temperature, said thermoplastic sleeve thereby melt forming during said squeezing and said sleeve conforming to said textured pattern without melting.

12. The method according to claim 11, wherein said diameter of said outer surface of said mandrel contracts about 0.00075" or less per side during said contracting step.

13. The method according to claim 12, wherein said material consists of aluminum, brass, copper, gold, magnesium, nickel, PVC, high durometer rubber, silver or stainless steel.

14. The method according to claim 1, wherein said mandrel comprises a solid tube made from a shape memory material having two-way shape memory, said diameter being in a larger remembered state during said squeezing step and said contracting step comprising cooling said tube below a transformation temperature to return said diameter to a smaller remembered state.

15. The method according to claim 14, wherein said contracting step comprises cooling said tube below room temperature to return said diameter to said smaller remembered state.

16. The method according to claim 14, further comprising heating said mandrel during said squeezing step, said heating raising the temperature of said shape memory material above said transformation temperature to return said diameter to said larger remembered state, said contracting step comprising cooling said tube to room temperature to return said diameter to said smaller remembered state.

17. The method according to claim 14, wherein said sleeve comprises a polymeric material, and further comprising disposing a thermoplastic sleeve over said sleeve and heating said sleeve and said thermoplastic sleeve while squeezing said sleeve and said thermoplastic sleeve during said squeezing step, wherein said thermoplastic sleeve has a first melting temperature lower than a second melting temperature of said sleeve, said sleeve and said thermoplastic sleeve being heated above said first melting temperature and below said second melting temperature, said thermoplastic sleeve thereby melt forming during said squeezing and said sleeve conforming to said textured pattern without melting.

18. The method according to claim 17, wherein said diameter of said outer surface of said mandrel contracts about 0.0025" or less per side during said contracting step.

19. The method according to claim 1, wherein said mandrel comprises a tube with a slot extending through a wall of said tube, said contracting step comprising reducing a width of said slot to contract said diameter.

20. The method according to claim 19, wherein said outer surface of said mandrel contacts at least 90% of said inner surface of said sleeve along said length of at least half said overall length of said self-expanding implant, said width of said slot is about 0.0015" or less during said squeezing step.

21. The method according to claim 20, further comprising an inner support member disposed through said tube during said squeezing step, said contracting step comprising removing said inner support member to allow said reducing of said width of said slot.

22. The method according to claim 21, wherein said diameter of said outer surface of said mandrel contracts about 0.0015" or less per side during said contracting step, said sleeve comprises a polymeric material, and further comprising disposing a thermoplastic sleeve over said sleeve and heating said sleeve and said thermoplastic sleeve while squeezing said sleeve and said thermoplastic sleeve during said squeezing step, wherein said thermoplastic sleeve has a first melting temperature lower than a second melting temperature of said sleeve, said sleeve and said thermoplastic sleeve being heated above said first melting temperature and below said second melting temperature, said thermoplastic sleeve thereby melt forming during said squeezing and said sleeve conforming to said textured pattern without melting.

* * * * *